(12) United States Patent
Mazeaud et al.

(10) Patent No.: US 9,303,256 B2
(45) Date of Patent: Apr. 5, 2016

(54) IMMOBILIZATION OF ENZYMES

(75) Inventors: Isabelle Mazeaud, Frederiksberg (DK); Poul Borge Rosenius Poulsen, Bagsvaerd (DK); Morten Wurtz Christensen, Lyngby (DK); Jesper Brask, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 1744 days.

(21) Appl. No.: 11/541,615

(22) Filed: Oct. 2, 2006

(65) Prior Publication Data

US 2007/0087418 A1    Apr. 19, 2007

Related U.S. Application Data

(60) Provisional application No. 60/724,862, filed on Oct. 7, 2005.

(30) Foreign Application Priority Data

Sep. 30, 2005  (DK) ................................. 2005 01368

(51) Int. Cl.
  *C12N 11/04*  (2006.01)
  *C12N 11/14*  (2006.01)

(52) U.S. Cl.
  CPC ..................................... *C12N 11/14* (2013.01)

(58) Field of Classification Search
  CPC .......... C12N 1/00; C12N 11/00; C12N 11/14; C12N 11/04; C12P 1/00
  See application file for complete search history.

(56) References Cited

U.S. PATENT DOCUMENTS

| 4,071,409 A | | 1/1978 | Messing et al. |
| 4,141,857 A | | 2/1979 | Levy et al. |
| 4,438,196 A | | 3/1984 | Lantero, Jr. |
| 4,749,653 A | * | 6/1988 | Lee et al. ...................... 435/176 |
| 4,888,285 A | | 12/1989 | Nishimura |
| 4,940,664 A | | 7/1990 | Mucke |
| 6,268,191 B1 | * | 7/2001 | Prud'homme et al. ....... 435/178 |
| 6,582,942 B1 | * | 6/2003 | Christensen et al. ......... 435/134 |

FOREIGN PATENT DOCUMENTS

| CA | 2 277 371 | 1/2001 |
| EP | 0133531 | 2/1985 |
| EP | 0206 687 | 12/1986 |
| EP | 0 216 272 | 5/1993 |
| EP | 0 641 859 | 3/1995 |
| WO | WO 95/22606 | 8/1995 |
| WO | WO 99/33964 | 7/1999 |

OTHER PUBLICATIONS

Magnan et al, Journal of Membrane Science, vol. 24, pp. 161-166 (2004).
Hwang et al, Biochemical Engineering Journal, vol. 17, pp. 85-90 (2004).
Linqui Cao, Chemical Biology, vol. 9, pp. 217-226 (2005).
Walter et al. Biotechnology Techniques vol. 3, (5) pp. 345-348 (1989).

\* cited by examiner

*Primary Examiner* — Robert Yamasaki
(74) *Attorney, Agent, or Firm* — Kristin McNamara

(57) ABSTRACT

The present invention relates to the immobilization of enzymes by adsorbing enzymes, a polyfunctional amine and a cross-linking agent onto a particulate porous carrier in a mixer apparatus or in a fluid bed apparatus.

15 Claims, No Drawings

IMMOBILIZATION OF ENZYMES

CROSS-REFERENCE TO RELATED APPLICATIONS

This application claims priority or the benefit under 35 U.S.C. 119 of Danish application no. PA 2005 01368 filed Sep. 30, 2005 and U.S. provisional application No. 60/724,862 filed Oct. 5, 2005, the contents of which are fully incorporated herein by reference.

FIELD OF THE INVENTION

The present invention relates to a process for producing an immobilized enzyme product, and the use of such immobilized enzyme products in continuous enzyme based processes such as in organic synthesis.

BACKGROUND OF THE INVENTION

Enzyme immobilization concerns immobilizing an enzyme product on a carrier on which the enzyme is fixed and yet functional and for which the enzyme is not liberated to the solvent to which it is applied. The most commonly immobilized enzymes are glucose isomerase used for isomerization reactions.

The industrial use of enzymes is often limited by their high cost and rapid inactivation. To improve their economic feasibility in industrial processes, enzymes are generally immobilized onto a matrix. Immobilization facilitates re-use of the enzymes, and may affect the selectivity and stability of the enzyme. Immobilization research has mainly focused upon means to enhance the transfer of enzymes onto the support, and upon means to ensure that the transferred enzymes remain active.

A number of different organic and inorganic support matrices and enzyme immobilization techniques have been tried with a view to achieve a high level of enzyme uptake with a minimum of enzyme degradation or inactivation.

A widely used approach to enzyme immobilization might be referred to as the covalent cross-linking process and is exemplified by U.S. Pat. No. 4,071,409 (Messing et al.). According to the teaching of this patent a support medium is modified or coated to present functionalities which can then be linked by way of a cross-linking agent to free functional groups of the enzyme.

In many industrial immobilization processes described in the prior art, the carrier or support material is placed in a column shaped adsorption vessel and an enzyme containing liquid is recirculated until sufficient adsorption of the enzyme on the carrier has been obtained. Following the adsorption step the column is emptied by manually shoveling the enzyme-carrier product into trays. The product is then dried by placing the trays under vacuum at room temperature for a period of 14-16 hours.

EP 0216272 describes a granular diatomaceous earth which is treated with a polyamine and reacted with e.g. glutaraldehyde, where after it is reacted with enzyme to form an immobilized enzyme. It is prepared in aqueous solution in a columnar reactor.

EP 0641859 describes a granular diatomaceous earth carrier which is treated with a polyamine. Further an amine reactive material is reacted with enzyme which is contacted with the carrier to form an immobilized enzyme. It is prepared in aqueous solution in a column.

U.S. Pat. No. 4,438,196 describes a carbon carrier which is reacted with a polyamine, the carrier is further reacted with a reactant and finally the enzyme to form an immobilized enzyme.

U.S. Pat. No. 4,141,857 describes the preparation of an enzyme support which is prepared by reacting a porous carrier with a polyamine and thereafter a reactant.

Other immobilization processes are described in WO 95/22606 (Pedersen et al.) and WO 99/33964 (Christensen et al.).

WO 95/22606 describes a process, wherein an enzyme containing liquid is brought in contact with porous silica carrier in an extruder or a granulation apparatus.

WO 99/33964 discloses an immobilization process wherein the immobilization is prepared in a fluid bed apparatus.

CA 2277371 describes a process for immobilization of an enzyme by incubating a siliceous support having surface hydroxyl groups with a first aqueous solution comprising a polyaldehyde and subsequently allowing a second aqueous solution comprising an enzyme to come into contact with the modified support and finally removing the support from the solution.

EP 133531 describes a process for immobilisation of an enzyme by (a) introducing into an aqueous medium containing an enzyme and a polyethyleneimine and (b) adding of glutaraldehyde and chitosan to the aqueous medium and subsequently removing the cross linked product from the liquid medium.

In U.S. Pat. No. 4,888,285 (Nishimura et al.) a silica gel is modified by reaction with an aminosilane derivative in an organic solvent. The resulting aminated support is then linked to the enzyme in the presence of glutaraldehyde, tannic acid and chitosan.

EP 0206687 discloses an immobilization process comprising mixing a dispersion of enzyme with polyazetidine prepolymer and glutaraldehyde followed by dewatering.

Immobilized enzymes are known to be used in continuous enzymatic reactions within a variety of industrial applications, including waste water treatment, production of pharmaceuticals and chemicals.

SUMMARY OF THE INVENTION

One object of the present invention is to provide a simple and efficient process for industrial immobilization of enzymes, which provides a product with increased amount of enzyme immobilized on the carrier and a product with less tendency to leach the enzyme during use in the end application.

The process of the invention has been found to surprisingly provide an immobilized enzyme product with a higher enzyme activity and with a decreased tendency to leach the enzyme during use in the end application compared to immobilized enzyme products obtained from known immobilization processes.

The present invention provides thus in a first aspect a process for producing an immobilized enzyme preparation comprising the following steps:
a) preparing a liquid medium comprising an enzyme;
b) preparing a liquid medium comprising a polyfunctional amine
c) preparing a liquid medium comprising a cross-linking agent;
d) introducing the liquid medium of a), b) and c) onto a particulate porous carrier;

Wherein the introducing of the liquid media of a), b) and c) onto the particulate porous carrier may be in any order or simultaneously and wherein the adsorption capacity of the carrier is not exceeded.

In a second aspect the present invention is directed to an immobilized enzyme product obtainable by the above described process.

DETAILED DESCRIPTION OF THE INVENTION

Introduction

Immobilization of enzymes has been known for many years. An immobilized enzyme product may be used in enzymatic modification of an organic compound such as in organic synthesis processes.

Immobilized enzymes prepared according to the invention have potential applications in a wide range of enzymatic employed processes such as in the production of pharmaceuticals, specialty commodity chemicals, waste water treatment and high fructose syrup production.

Normally an immobilized enzyme product used in said processes may be reused several times. However if the immobilized enzyme product is leaching, which result in an activity decrease in enzyme activity of the immobilized enzyme product over time, the enzyme product can not be reused as many times as desired. Furthermore a problem with leaching of enzyme during use of immobilized enzyme products is that the leached enzyme will be present in the product of the organic synthesis which is not desirable.

The invention described herein is a process for immobilization of an enzyme. The process includes impregnating a suitable carrier with an enzyme, a polyfunctional amine and a cross-linker.

The immobilized enzyme system comprises in a particular embodiment:
  A particulate carrier with a high physical strength in order to be utilized in continuously packed bed reactors as well as in continuously stirred tank reactors;
  An enzyme;
  A polyfunctional amine.
  A crosslinking agent.

The function of the polyfunctional amine is to provide a network of amine-groups available for covalent cross-linking with the cross-linking agent and the enzymes amine-groups. The polyfunctional amine will provide a mechanical strength to the immobilized enzyme product and improve the overall cross-linking of the enzyme and thereby minimize the leaching of enzyme from the carrier to which the polyfunctional amines has been loaded.

The cross-linking agent is a poly or bis-functional reagent that reacts with the polyfunctional amine and the enzyme to produce covalent cross-linking. The cross-linking agent can also react intermolecular in between the polyfunctional amines as well as in between the enzymes.

A binder may also be introduced e.g. before cross-linking to minimize abrasion from the silica particle surface.

It has surprisingly been found that through the present process it is possible to obtain an immobilized enzyme product which initially has a higher enzyme activity and furthermore leaches less than known immobilized enzymes. An important aspect of the invention is that the immobilization processes can be easily scaled up by applying other larger standard equipment. Thus the equipment setting ranges given vide supra may be adjusted to optimize larger scale equipment.

The Carrier

The carrier is in one embodiment of the present invention a solid carrier. In another embodiment of the present invention the carrier is a porous carrier.

The carrier of the present invention is in one embodiment of the present invention a particulate porous material. The particles making up the particulate porous material may suitably have a diameter in the range of 50-1500 µm such as 100-1000 µm, preferably 250-700 µm; have a surface area of 5-1000 $m^2$/g, 20-1000 $m^2$/g, in particular 100-700 $m^2$/g, more particular 10-300 $m^2$/g, and have a pore size of 5 nm-50 µm, such as 5 nm-1000 nm, in particular 10-500 nm, more particular 100-300 nm. In a particular embodiment of the present invention the particle size of the particles making up the particulate porous material is 100-600 µm. In a more particular embodiment of the present invention the particle size of the particles making up the particulate porous material is 150-500 µm. In an even more particular embodiment of the present invention the particle size of the particles making up the particulate porous material is 200-450 µm. In a most particular embodiment of the present invention the particle size of the particles making up the particulate porous material is 250-400 µm.

The carrier particles may comprise inorganic, organic or both inorganic and organic material. Said carrier may further have a hydrophilic or hydrophobic surface.

In a first embodiment of the present invention the carrier particles comprise an inorganic material with a substantially hydrophilic surface, which is essentially insoluble in hydrophilic or hydrophobic liquids or mixtures thereof. Carriers may be based on silicas (e.g. Sipernat 2200 from Degussa, Germany), zeolites (e.g. Wessalith MS330 from Degussa, Germany), aluminas, diatomaceous earth, ceramics such as disclosed in Yoshihiko Hirose et Al., Proceedings from 3rd International Symposium on Biocatalysis and Biotransformations, La Grande Motte, France, 1997, p 238) and kaolins (e.g. kaolin's subjected to acid, hydrothermal and baking treatment as disclosed in U.S. Pat. No. 5,614,401). In a particular embodiment of the present invention the particulate porous carrier is selected from the group consisting of silica, zeolite, alumina, ceramic and kaolin.

In a particular embodiment of the present invention carrier may be metal oxides such as alumina, particularly gamma alumina, silica, zirconia, silica magnesia, silica-zirconia-alumina etc.

In a second embodiment of the present invention the carrier particles comprise a hydrophilic inorganic material as described in the first embodiment coated with organic moieties thus having a substantially hydrophobic surface, e.g. as described in JP 09000257-A, wherein an acid treated kaolin carrier is coated with N-phenyl-gamma-aminopropyltrimethoxysilane. Further carriers are described in JP 08126489-A, wherein a water insoluble carrier is coated with a polymer forming a disulphide linkage with enzymes. In a third embodiment of the invention the carrier particles comprise an organic polymer resin. The resin may be an adsorbent resin, preferably a polyacrylate, a polymethacrylate (e.g. polymethyl methacrylate), polystyrene cross-linked with divinylbenzene, polyurethane or polypropylene or the resin may be an ion exchange resin, preferably an anion exchange resin, e.g. a weakly basic anion exchange resin. A preferred anion exchange resin is a phenolic type Duolite resin from Rohm & Haas.

Further the carrier may be made from regenerated chitosan as disclosed in DE 4429018-A.

Enzymes

The enzyme to be immobilized according to the invention may be any enzyme suitable for use in enzyme based processes.

The enzyme in the context of the present invention may be any enzyme or combination of different enzymes. Accordingly, when reference is made to "an enzyme" this will in general be understood to include one enzyme or a combination of enzymes. Thus the immobilized enzyme product of the invention may comprise several different enzymes.

It is to be understood that enzyme variants (produced, for example, by recombinant techniques) are included within the meaning of the term "enzyme". Examples of such enzyme variants are disclosed, e.g. in EP 251,446 (Genencor), WO 91/00345 (Novo Nordisk), EP 525,610 (Solvay) and WO 94/02618 (Gist-Brocades NV).

Enzymes can be classified on the basis of the handbook Enzyme Nomenclature from NCIUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUBMB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy(ModO) internet site (Coutinho, P. M. & Henrissat, B. (1999) Carbohydrate-Active Enzymes server at URL:

http://afmb.cnrs-mrs.fr/~cazy/CAZY/index.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation", K. Ohmiya, K. Hayashi, K. Sakka, Y. Kobayashi, S. Karita and T. Kimura eds., Uni Publishers Co., Tokyo, pp. 15-23).

The types of enzymes which may be incorporated in granules of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1), laccases (EC 1.10.3.2) and glucose oxidases (EC 1.1.3.4)]. An Example of a commercially available oxidoreductase (EC 1.-.-.-) is Gluzyme™ (enzyme available from Novozymes A/S). Further oxidoreductases are available from other suppliers. Preferred transferases are transferases in any of the following sub-classes:

a Transferases transferring one-carbon groups (EC 2.1);
b transferases transferring aldehyde or ketone residues (EC 2.2); acyltransferases (EC 2.3);
c glycosyltransferases (EC 2.4);
d transferases transferring alkyl or aryl groups, other that methyl groups (EC 2.5); and
e transferases transferring nitrogenous groups (EC 2.6).

A most preferred type of transferase in the context of the invention is a transglutaminase (protein-glutamine γ-glutamyltransferase; EC 2.3.2.13).

Further examples of suitable transglutaminases are described in WO 96/06931 (Novo Nordisk A/S).

Preferred hydrolases in the context of the invention are: carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases.

In the present context, the term "carbohydrase" is used to denote not only enzymes capable of breaking down carbohydrate chains (e.g. starches or cellulose) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses):

α-amylases (EC 3.2.1.1), β-amylases (EC 3.2.1.2), glucan 1,4-α-glucosidases (EC 3.2.1.3), endo-1,4-beta-glucanase (cellulases, EC 3.2.1.4), endo-1,3(4)-β-glucanases (EC 3.2.1.6), endo-1,4-β-xylanases (EC 3.2.1.8), dextranases (EC 3.2.1.11), chitinases (EC 3.2.1.14), polygalacturonases (EC 3.2.1.15), lysozymes (EC 3.2.1.17), β-glucosidases (EC 3.2.1.21), α-galactosidases (EC 3.2.1.22), β-galactosidases (EC 3.2.1.23), amylo-1,6-glucosidases (EC 3.2.1.33), xylan 1,4-β-xylosidases (EC 3.2.1.37), glucan endo-1,3-β-D-glucosidases (EC 3.2.1.39), α-dextrin endo-1,6-α-glucosidases (EC 3.2.1.41), sucrose α-glucosidases (EC 3.2.1.48), glucan endo-1,3-α-glucosidases (EC 3.2.1.59), glucan 1,4-β-glucosidases (EC 3.2.1.74), glucan endo-1,6-α-glucosidases (EC 3.2.1.75), galactanases (EC 3.2.1.89), arabinan endo-1, 5-α-L-arabinosidases (EC 3.2.1.99), lactases (EC 3.2.1.108), chitosanases (EC 3.2.1.132), glucose isomerases (EC 5.3.1.9) and xylose isomerases (EC 5.3.1.5).

The most commonly used enzymes to be immobilized are glucose isomerases and lipases.

Glucose isomerases: suitable glucose isomerases include those of bacterial or fungal origin. Chemically modified or protein engineered mutants are included.

Lipases: Suitable lipases include those of bacterial or fungal origin. Chemically modified or protein engineered mutants are included. Examples of useful lipases include lipases from *Candida*, or *Rhizomucor*, *C. Antarctica*, *R. miehei*, *Hyphozyma*, *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422). The lipase may be positionally site specific (i.e. 1,3 specific) or non-specific, upon interaction with triglycerides as substrates.

Furthermore, a number of cloned lipases may be useful, including the *Penicillium camembertii* lipase described by Yamaguchi et al., (1991), Gene 103, 61-67), the *Geotricum candidum* lipase (Schimada, Y. et al., (1989), J. Biochem., 106, 383-388), and various *Rhizopus* lipases such as a *R. delemar* lipase (Hass, M. J et al., (1991), Gene 109, 117-113), a *R. niveus* lipase (Kugimiya et al., (1992), Biosci. Biotech. Biochem. 56, 716-719) and a *R. oryzae* lipase.

Other types of lipolytic enzymes such as cutinases may also be useful, e.g. a cutinase derived from *Pseudomonas mendocina* as described in WO 88/09367, or a cutinase derived from *Fusarium solani pisi* (e.g. described in WO 90/09446). In a particular embodiment of the present invention the enzyme used to partly replace or fully replace surfactants is a cutinase, in a more particular embodiment the enzyme used to partly or fully replace surfactants are derived from *Pseudomonas mendocina* or *Fusarium solani pisi*.

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Examples of commercially available lipases include Lipex, Lipoprime™, Lipolase™, Lipolase™ Ultra, Lipozyme™, Palatase™, Novozym™ 435 and Lecitase™ (all available from Novozymes A/S).

Other commercially available lipases include Lumafast™ (*Pseudomonas mendocina* lipase from Genencor International Inc.); Lipomax™ (*Ps. pseudoalcaligenes* lipase from DSM/Genencor Int. Inc.; and *Bacillus* sp. lipase from Genencor enzymes. Further lipases are available from other suppliers.

Examples of commercially available carbohydrases include Alpha-Gal™, Bio-Feed™ Alpha, Bio-Feed™ Beta, Bio-Feed™ Plus, Bio-Feed™ Plus, Novozyme™ 188, Celluclast™, Cellusoft™, Ceremyl™, Citrozym™, Denimax™, Dezyme™, Dextrozyme™, Finizym™, Fungamyl™, Gamanase™, Glucanex™, Lactozym™, Maltogenase™, Pentopan™, Pectinex™, Promozyme™, Pulpzyme™, Novamyl™, Termamyl™, AMG™ (Amyloglucosidase Novo), Maltogenase™, Sweetzyme™ and Aquazym™ (all available from Novozymes A/S). Further carbohydrases are available from other suppliers, such as the Roxazyme™ and Ronozyme™ product series (DSM Nutritional Products), the Avizyme™, Porzyme™ and Grindazyme™ product series (Danisco, Finnfeeds), and Natugrain™ (BASF).

Proteases: Suitable proteases include those of animal, vegetable or microbial origin. Microbial origin is preferred. Chemically or genetically modified or protein engineered variants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583. In a particular embodiment the detergent composition comprises proteases derived from *Bacillus*, e.g. *Bacillus Clausii, Bacillus Lentus, Bacillus halmapalus* and *B. amyloliquefaciens*.

In a particular embodiment of the present invention the enzyme used to partly replace or fully replace builders in detergent compositions are proteases derived from *Bacillus*, particularly proteases derived from microorganisms selected from the group consisting of *Bacillus Clausii, B. amyloliquefaciens, Bacillus halmapalus* and *B. lentus*.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Examples of commercially available proteases (peptidases) include Kannase™, Everlase™, Esperase™, Alcalase™, Neutrase™, Durazym™, Savinase™, Ovozyme™, Pyrase™, Pancreatic Trypsin NOVO (PTN), Bio-Feed™ Pro and Clear-Lens™ Pro (all available from Novozymes A/S, Bagsvaerd, Denmark). Other preferred proteases include those described in WO 01/58275 and WO 01/58276.

Other commercially available proteases include Ronozyme™ Pro, Maxatase™, Maxacal™, Maxapem™, Opticlean™, Propease™, Purafect™ and Purafect Ox™ (available from Genencor International Inc., Gist-Brocades, BASF, or DSM Nutritional Products).

Other commercially available enzymes include Pectaway™, and Stainzyme™.

Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Natalase™, Stainzyme™, Duramyl™, Termamyl™, Termamyl™ Ultra, Fungamyl™ and BAN™ (Novozymes A/S), Rapidase™, Purastar™ and Purastar OXAM™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, Endolase™, Renozyme™ and Carezyme™ (Novozymes A/S), Clazinase™, and Puradax HA™ (Genencor International Inc.), and KAC-500(B)™ (Kao Corporation).

Oxidoreductases: Particular oxidoreductases in the context of the invention are peroxidases (EC 1.11.1), laccases (EC 1.10.3.2) and glucose oxidases (EC 1.1.3.4)]. An Example of a commercially available oxidoreductase (EC 1.-.-.-) is Gluzyme™ (enzyme available from Novozymes A/S). Further oxidoreductases are available from other suppliers.

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

Mannanase: Any mannanase suitable for use in alkaline solutions can be used. Suitable mannanases include those of bacterial or fungal origin. Chemically or genetically modified mutants are included.

In a preferred embodiment the mannanase is derived from a strain of the genus *Bacillus*, especially *Bacillus* sp. 1633 disclosed in positions 31-330 of SEQ ID NO:2 or in SEQ ID NO: 5 of WO 99/64619 or *Bacillus agaradhaerens*, for example from the type strain DSM 8721. In a more preferred embodiment of the present invention the mannanase is derived from *Alkalophilic bacillus*. Suitable mannanases include Mannaway™ (Novozymes A/S).

Pectate lyase: Any pectate lyase suitable for use in alkaline solutions can be used. Suitable pectate lyases include those of bacterial or fungal origin. Chemically or genetically modified mutants are included.

In a preferred embodiment the pectate lyase is derived from a strain of the genus *Bacillus*, especially a strain of *Bacillus substilis*, especially *Bacillus subtilis* DSM14218 disclosed in SEQ ID NO:2 or a variant thereof disclosed in Example 6 of WO 02/092741. In a more preferred embodiment of the present invention the pectate lyase is derived from *Bacillus licheniformis*.

Examples of commercially available phytases include Bio-Feed™ Phytase (Novozymes), Ronozyme™ P (DSM Nutritional Products), Natuphos™ (BASF), Finase™ (AB Enzymes), and the Phyzyme™ product series (Danisco). Other preferred phytases include those described in WO 98/28408, WO 00/43503, and WO 03/066847.

In a particular embodiment the enzyme is selected from the group consisting of hydrolases, cutinases, oxidases transferases, reductases, hemicellulases, esterases, isomerases, pectinases, lactases, peroxidases, laccases, pectinases, catalases, nitrilases and mixtures thereof.

In another particular embodiment of the present invention the hydrolases is selected from the group consisting of proteases, amylases, lipases, phospholipases, esterases, mannanases, cellulases and mixtures thereof.

In a more particular embodiment of the present invention the enzymes are selected from the group consisting of proteases, lipases, glycosidases, oxidoreductases, oxidases, ketoisomerases and esterases.

The Liquid Medium Comprising an Enzyme

The enzyme containing liquid medium is in a particular embodiment a hydrophilic medium, preferably aqueous. It may contain other organic or biological matter. Thus it may be a fermentation broth or an enzyme concentrate solution obtainable by purifying a fermentation broth by e.g. ultra filtration or by protein precipitation, separation and re-dissolution in another aqueous medium. It may further be substantially pure enzyme dissolved in an aqueous medium. In a special embodiment of the present invention the enzyme containing aqueous liquid has not been subjected to costly processing steps prior to immobilization to remove water such as evaporation nor has it been subjected to addition of non aqueous solvents, e.g. organic solvents such as alcohols, e.g. (poly)ethylene glycol and/or (poly)propylene glycol.

In a particular embodiment of the present invention the liquid medium comprising the enzyme is also the liquid medium comprising the polyfunctional amine.

The liquid medium is preferably prepared by adding an aqueous solution of polyfunctional amine to an aqueous liquid comprising the enzyme.

The Liquid Medium Comprising Polyfunctional Amine

The liquid comprising the polyfunctional amine may be a hydrophilic medium, preferably aqueous.

The polyfunctional amine may be any polyfunctional amine known in the art.

Suitable polyfunctional amines may be but are not limited to the group selected from polyethylene imines (PEI), polyethylenediamine, polymetylenedicyclohexylamine, polymetylenedianiline, polytetraethylenepentamine, polyphenylenediamine, polypropylenimine, polyallylamine, polyvinylamine or polymers of 1-amino ethylene with or without N-vinyl formamide (as described in EP 502035-B1), chitosan, albumin, gelatine. Other suitable amines may be spermidine, spermine, triethylenetetramine, polypropyleneimine dendrimers and bis(2-ethylamino)-1,3-propanediamine and mixtures thereof. Amines can be primary, secondary, tertiary or quaternary.

PEI is a weak, polybasic aliphatic amine, which can be branched or linear. The polyethyleneimine may be of any suitable molecular weight. In a particular embodiment the mole weight is 20.000 to 80.000. In a more particular embodiment the mole weight is 40.000 to 60.000. Polyethylene imines of differing molecular weight are obtainable from BASF (Polymin), Cordova Chemical company (Corcat P) and Nipon shokubai Kagaku Kogyo (Epomin).

The liquid medium may contain other organic or biological matter.

The enzyme protein—polyfunctional amine ratio is in a particular embodiment 1:20 to 20:1, 1:15 to 15:1, 1:5 to 5:1, in another embodiment the ratio is 1:2 to 3:1, in a further embodiment the ratio is 1:1 to 2:1 based on 100 solution.

The pH of the liquid is preferably 4-11. In a particular embodiment of the present invention the pH of the liquid is above 6. In another particular embodiment the pH of the liquid is above 7. In a further embodiment the pH of the liquid is above 7.5.

The Liquid Medium Comprising a Cross-Linking Agent

The cross-linking agent may be any compound capable of cross linking with the chosen enzyme.

The cross-linking agent may be selected from the group consisting of but are not limited to polyfunctional aldehydes, polyfunctional organic halides, polyfunctional anhydrides, polyfunctional azo compounds, polyfunctional isothiocyanates, polyfunctional isocyanates and mixtures thereof. In a particular embodiment of the present invention the cross-linking agent is succindialdehyde, terephthaldehyde, bis-diazobenzidine-2,2'disulfonic acid, glutaraldehyde, polyazetidine, cyanuric chloride, biepoxides, diisocyanates e.g. toluylene diisocyanate, hexamethylene diisocyanate. In a particular embodiment of the present invention the cross-linker is glutaraldehyde and/or polyazetidine.

The liquid medium comprising a cross-linker is preferably a hydrophilic medium, preferably aqueous. It may contain other organic or biological matter. The enzyme protein-cross-linking agent ratio (based on 100% solution) may be 1:20 to 1:0-05, such as 1:10 to 1-0.1, in a particular embodiment the ratio is 1:6 to 1:0.4, in another particular embodiment the ratio is 1:3 to 1:0.4.

The liquid media may further comprise a component which enables the enzyme, the polyfunctional amine or the cross-linking agent to better stick to the particulate porous carrier. The component may be any binder known in the art.

Suitable components may be salts, carbohydrates e.g. starches, polymers and waxes.

In a particular embodiment of the present invention the component is dextrin polyvinylpyrrolidone sorbitol, polyethylene glycol, metal silicates or metal orthosilicates.

The component may be added to any of the liquid media.

The Immobilization Process

The immobilization process is in one embodiment of the invention a process for producing an immobilized enzyme preparation comprising the following steps:

a) preparing a liquid medium comprising an enzyme;
b) preparing a liquid medium comprising a polyfunctional amine;
c) preparing a liquid medium comprising a cross linking agent;
d) introducing the liquid medium of a), b) and c) onto a particulate porous carrier Wherein the introducing of the liquid media of a), b) and c) onto the particulate porous carrier may be in any order or simultaneously and wherein the adsorption capacity of the carrier is not exceeded.

In one embodiment of the present invention the liquid medium comprising a polyfunctional amine and the liquid medium comprising the enzyme is one and the same liquid.

In another embodiment the liquid medium comprising an enzyme and the liquid medium comprising a polyfunctional amine is added to the particulate porous carrier before the liquid comprising the cross-linking agent is added.

In a further embodiment of the present invention the liquid comprising the crosslinking agent is added to the particulate carrier before the liquid/liquids comprising the enzyme and the polyfunctional amine.

With the term "adsorption capacity of the carrier" is meant the amount of liquid the carrier is able to adsorb.

One way to determine the adsorption capacity is to dry a sample of carrier at 105° C. for 24 hrs., cool the carrier down to ambient temperature and place 1 g of the dried carrier material in 100 ml liquid at 20° C. for 1 hour, then the carrier is separated from the excess liquid by drainage and the weight of the carrier comprising the adsorbed liquid is determined.

When the adsorption capacity is exceeded the carrier is not able of adsorbing any more liquid, and if more liquid is present it will be called excess liquid.

Thus in immobilization processes taking place in a liquid medium e.g. in a column, the limit for the carriers adsorption capacity has been exceeded and excess liquid is present.

In a particular embodiment the amount of liquid added to the process is not resulting in the adsorption capacity of the carrier being exceeded. The amount of liquid added to the process should be limited so the adsorption capacity of the carrier is not exceeded. In a particular embodiment of the present invention the liquid should be added in such amounts that substantially no agglomeration of the carrier occurs.

In a first embodiment of the present invention the ratio of the weight of liquid medium added to the process and the weight of the carrier is below 50. In a second embodiment of the present invention the ratio of the weight of liquid medium added to the process and the weight of the carrier is below 25. In a third embodiment the ratio of liquid medium to carrier is below 10. In a further embodiment the ratio is below 5.

In another embodiment of the invention an additional process step e) is taking place. In step e) the volatile components are removed from the resulting product. The removing of volatile components in step e) may be performed by, but is not limited to, various methods such as filtration, centrifugation, spray-drying, air-drying and freeze-drying. In a particular embodiment step e) is conducted in a fluidized bed. Suitable temperatures of the inlet air for removing volatile components will primarily depend of the thermal stability of the enzyme (the inactivation temperature). The temperature may be 40-130° C., 40-90° C., such as 50-70° C., e.g. 60° C. A higher temperature provides shorter immobilization and drying times.

The immobilization process is in another embodiment of the invention a process for producing an immobilized enzyme preparation comprising the following steps:

a) preparing a liquid medium comprising an enzyme and a polyfunctional amine;
b) preparing a liquid medium comprising a cross linking agent;
d) introducing the liquid medium of a) and b) onto a particulate porous carrier and
wherein the introducing of the liquid media of a) and b) onto the particulate porous carrier may be in any order or simultaneously.

The immobilization process may be performed in any apparatus suitable for said process.

In a particular embodiment of the present invention he apparatus is selected from the group consisting of mixers, fluid beds and pan coaters.

In a particular embodiment of the present invention the immobilization process is performed in a mixer apparatus, a fluid bed or a pan coater.

The mixer apparatus of the present invention may be any mixer apparatus e.g. a Lödige Mixer, Germany. Immobilizing the enzyme on the carrier in a mixer may suitably be conducted at ambient temperature. Mixing times may suitably be 5-60 minutes, preferably 10-30 minutes.

The fluid bed apparatus may be any apparatus principally working as a fluid bed. The liquid media of the present invention may be introduced onto the carrier by atomization.

A suitable air inlet flow in the fluid bed equipment will depend on the size and density of the immobilized enzyme product, the amount of carrier and the fluid bed equipment. Further the air inlet flow has an upper limit, as the flow should be sufficient to keep the immobilized enzyme product fluidized, but not so powerful as to "blow off" the immobilized enzyme product.

When using a fluid bed for immobilization and drying simultaneously, the drying process will occur for as long as the liquid media are atomized into the fluid bed, and may suitably be extended for 5-30 minutes after inlet of the liquid media have ended.

Further, time consumption for immobilization and/or drying of the immobilized enzyme product when equipment, air inlet flow and air temperature are fixed will depend on the quantity of the enzyme, the polyfunctional amine and the cross-linking agent and the carrier. An important aspect of the invention is that the immobilization processes can be easily scaled up by applying other larger standard equipment. Thus the equipment setting ranges given vide supra may be adjusted to optimize larger scale equipment.

Immobilization of Enzyme on Carriers with a Hydrophilic Surface:

In a particular embodiment of the present invention the carrier has a substantially hydrophilic surface. In a particular embodiment the immobilization process may be conducted in a standard mixing equipment (e.g. Lödiger, Germany), wherein the liquid media of step a), b) and c) are introduced by atomization to the dry porous and particulate carrier during mixing, e.g. using a nebulizer connected to a pump (e.g. a standard peristaltic Watson-Marlow pump).

In another particular embodiment of the present invention the immobilization of enzyme on a carrier having a substantially hydrophilic surface may alternatively be conducted in a standard fluid bed equipment, e.g. a Uni-Glatt fluidized bed apparatus (Glatt, Germany), wherein the dry porous and particulate carrier is fluidized and the liquid media of step a), b) and c) are introduced by atomization to the fluidized carrier, e.g. using a nebulizer connected to a pump (e.g. a standard peristaltic Watson-Marlow pump). In this embodiment immobilization and drying may be conducted simultaneously.

Immobilization on Carriers with a Hydrophobic Surface:

In a particular embodiment of the present invention the immobilization of enzyme on a carrier having a substantially hydrophobic surface may be conducted in a standard mixing equipment, wherein the liquid media of step a), b) and c) are introduced to the dry porous and particulate carrier In another particular embodiment of the invention the immobilization of enzyme on a carrier having a substantially hydrophobic surface may alternatively be conducted in a standard fluid bed equipment, e.g. a Uni-Glatt fluidized bed apparatus (Glatt, Germany), wherein the dry porous and particulate carrier is fluidized and the liquid media of step a), b) and c) are introduced by atomization to the fluidized carrier, e.g. using a nebulizer connected to a pump (e.g. a standard peristaltic Watson-Marlow pump). In this embodiment immobilization and drying are conducted simultaneously.

In one embodiment of the present invention the immobilization process is not taking place in a liquid medium such as in a column comprising apparatus.

Uses of the Immobilized Enzyme Preparation

Immobilized enzymes prepared in the context of the invention may be used for hydrolysis, synthesis or modification of organic substances. The hydrolysis, synthesis or modification preferably takes place in a medium essentially devoid of free water.

Accordingly the invention encompasses a process for enzymatic modification of an organic compound comprising contacting in a reaction medium said organic compound with an immobilized enzyme produced according to the invention.

Immobilized cellulases can be used in both textile treatment (depilling of cotton and stone-washing of denim fabric) and deinking of recycled paper.

Immobilised glucose isomerase can be used as a catalyst for the production of high fructose syrup from glucose. Immobilized lactase can be used for foodstuff modification, such as removing lactose from milk.

Immobilized proteases can be used for preventing microbial growth on the surfaces of or as mild skin exfoliating applications.

Immobilized glucose oxidase can be used as a reagent for glucose assays, for the removal of oxygen from foodstuffs, or for the production of gluconic acid and its salts.

The immobilized enzyme of the present invention may be used for enzymatic modification of an organic compound comprising contacting in a reaction medium said organic compound with an immobilized enzyme produced by the process of the invention.

In a particular embodiment of the present invention the modification is an esterification reaction comprising contacting a first reactant which is a carboxylic acid and a second reactant which is an alcohol with an immobilized lipase produced by the process of the invention. The carboxylic acid may be selected from but not limited to the group consisting of fatty acids, lactic acid, benzoic acid, acrylic acid and methacrylic acid and the alcohol may be selected from but not limited to the group consisting of methanol, ethanol, isopropanol, polyols such as glycerol, sorbitol, isosorbide, xylitol, glucosides such as ethyl and methyl glucosides, neopentyl alcohol and propylene glycol.

In an embodiment the modification is a chiral resolution including an enantioselective synthesis or hydrolysis of carboxylic acid ester or amides.

In an embodiment the modification is an aldol condensation reaction between two aldehydes.

In a particular embodiment the modification is an epoxidation of olefinic groups by percarboxylic acid produced in situ by the enzyme in this present invention.

In a particular embodiment the modification is a polyesterification reaction wherein the organic compound to be modified is a hydroxycarboxylic acid or oligomers of such compound e.g. lactic acid or 3-hydroxypropanoic acid. Or the carboxylic acid is a dicarboxylic acid selected from the group consisting of adipic acid, succinic acid, fumaric acid, 2,5-furandicarboxylic acid, glucaric acid, terephthalic acid and isophthalic acid, and the second reactant is selected from the group consisting of polyols such as (1,4-butanediol, 1,6-hexanediol, glycerol, sorbitol, isosorbide, neopentyl alcohol, propylene glycol).

In another particular embodiment the modification is a ring opening polymerization reaction comprising contacting a lactone with an immobilized lipase produced by the present process.

Prepared Polymers may be Homo or Hetero Polymers.

In a particular embodiment the modification is a transesterification reaction comprising contacting a first reactant which is a carboxylic acid ester and a second reactant which is an alcohol with an immobilized lipase produced by the present process.

In a particular embodiment the modification is an interesterification reaction comprising contacting a first reactant which is a carboxylic acid ester and a second reactant which is a second carboxylic acid ester with an immobilized lipase produced by the present process. In a more particular embodiment the modification is an interesterification reaction comprising contacting a first reactant which is a polycarboxylic acid ester and a second reactant which is a second polycarboxylic acid ester, with an immobilized lipase produced by the present process.

The carboxylic acid ester may be selected from but not limited to the group consisting of alkyl esters of fatty acids, lactic acid, glucaric acid, benzoic acid, acrylic acid, methacrylic acid and wherein the alkyl may be methyl, ethyl, butyl and the alcohol may be selected from the group consisting of but not limited to methanol, ethanol, isopropanol, polyols such as glycerol, alkyl glucosides, such as ethyl glucoside or methyl glucoside, sorbitol, silicone and silicone derivatives, isosorbide, neopentyl alcohol and propylene glycol.

In a particular embodiment the modification is a hydrolysis or synthesis producing an enantiopure compound with an immobilized enzyme produced by the present.

In a particular embodiment the modification is an aldol condensation producing a compound with an immobilized lipase produced by the present process.

In a particular embodiment the modification is an amidation reaction comprising contacting a first reactant which is a carboxylic acid and a second reactant which is an amine with an immobilized lipase produced by the present process.

In a particular embodiment the modification is an epoxidation reaction comprising in situ production of epoxidation agent with an immobilized enzyme produced by the present process.

In an embodiment of the present invention an immobilized lipase enzyme is used for an esterification, transesterification or interesterification process in a medium essentially devoid of free water. The transesterification may be used for fatty acid substitution, comprising contacting a first reactant and a second reactant with said immobilized lipase by which a substitution reaction occurs.

The first reactant may be a fatty acid ester, preferably a triglyceride or a mixture of triglycerides. The second reactant may be another fatty acid ester different from the first reactant, preferably a triglyceride or a mixture of triglycerides. Further the second reactant may be an alcohol or a free fatty acid.

The medium in this preferred embodiment of the invention comprises an organic solvent, or it may consist essentially of triglycerides.

Said use of the invention may be applied in production of food products e.g. margarine or cocoa-butter substitutes.

The present invention is further described by the following examples which should not be construed as limiting the scope of the invention.

EXAMPLES

Example 1

Immobilization of Lipase on a silica based carrier with an enzyme protein load of 30 mg/g by a 1-step impregnation.
1. 3.0 kg of a solution of Lipase B from *Candida Antarctica* (18400 LU(CA)/g) was adjusted to pH 7.5±0.2 using 10% NaOH solution and diluted with 660 g of water. 129 g of disodium hydrogen phosphate were added to the enzyme solution and stirred until dissolution of the disodium hydrogen phosphate. The pH was adjusted back to pH 7.5±0.2 using 10% NaOH solution
2. The liquid Lipase solution (according to 1) was then applied uniformly onto 2.1 kg of Sipernat 2200 (silica based carrier from Degussa, Germany) in a 20 L mixer (Lödige, Germany) using continuous mixing with a rotating speed of 150 rpm at ambient temperature. An atomizing nozzle was used, which was adjusted to a 16 min spraying time.
3. After addition of the liquid lipase solution (According to 2), the carrier particles were dried in a fluidized bed (GEA) with inlet temperature 100° C. until the product temperature reached 60° C. A moisture content below 5% was thus obtained.

Activity of the immobilized enzyme product: 3600 PLU.
Enzyme protein leaching measured in dimethyl sulfoxide (DMSO): 30 mg/g
Enzyme protein level before leaching: 30 mg/g.

Measurement of Enzyme Activity:

Enzyme activity (LU=Lipase Unit) of liquid lipases is determined by Novozymes Standard Method EB-SM-0095.02 and is available on request from Novozymes A/S.

1 LU corresponds to the amount of enzyme which releases 1 µmol titrateable butyric acid/minute at standard conditions.

Enzyme activity (PLU=Propyl Laurate Unit) of immobilized lipase is determined by Novozymes Standard Method EB-SM-1069.02 and is available on request from Novozymes A/S. One PLU unit corresponds to 1 µmol/g/min, e.g. 1 µmol propyl laurate formed per g of enzyme per minute. The immobilised lipase esterify lauric acid with 1-propanol, forming propyl laurate. The activity (µmol/g/min) is determined by quantification of formed propyllaurate and consumed lauric acid by GC.

Leaching Measurements:

Immobilized enzyme (50 mg) is weighed into an Eppendorf tube to which DMSO (1 mL) is added. The mixture is incubated at 37° C. and 1200 rpm for 30 min. The DMSO supernatant is transferred to a microtiter plate and diluted (10x) with DMSO. Protein content is determined from the Coomassie (Bradford) Protein Assay, using a standard curve prepared from purified CaLB enzyme. Leaching is calculated as mg CaLB per g total weight.

Example 2

Immobilization of Lipase on a silica based carrier with an enzyme protein load of 30 mg/g by a 1-step impregnation and subsequent cross-linking by glutaraldehyde (GA)/polyethylene imine (PEI).
1. 3.0 kg of a solution of Lipase B from *Candida Antarctica* (18400 LU(CA)/g) was adjusted to pH 7.5±0.2 using 10% NaOH solution. 466 g of 15% polyethylene Imine aqueous solution (Sedipur, BASF) and 129 g of disodium hydrogen phosphate were added to the enzyme solution and stirred until dissolution of the disodium hydrogen phosphate. The pH was adjusted back to pH 7.5±0.2 using 10% NaOH solution.
2. The liquid Lipase solution (according to 1) was then applied uniformly onto 1.9 kg of Sipernat 2200 (silica based carrier from Degussa, Germany) in a 20 L mixer (Lodige, Germany) using continuous mixing with a rotating speed of 150 rpm at ambient temperature. An atomizing nozzle was used, which was adjusted to a 14 min spraying time.
3. After addition of the liquid lipase solution (According to 2), 933 g of 15% Glutaraldehyde aqueous solution (Dow) were then applied on the same silica carrier particles using the same rotating speed and a spraying time of 11 min.

After the treatment, the carrier particles were still free flowing individual particles due to the adsorption of the PEI containing-liquid enzyme solution and GA onto the carrier particles.
4. Finally, the carrier particles were dried in a fluidized bed (GEA) with inlet temperature 100° C. until the product temperature reached 60° C. A moisture content below 5% was thus obtained.

Activity of the immobilized enzyme product: 3200 PLU
Enzyme protein leaching measured in DMSO: 13 mg/g
Enzyme protein level before leaching: 30 mg/g

Example 3

Immobilization of Lipase on a silica based carrier with an enzyme protein load of 50 mg/g by a 2-step impregnation and subsequent cross-linking by glutaraldehyde (GA)/polyethylene imine (PEI).
1. 3.0 kg of a solution of Lipase B from *Candida Antarctica* (18400 LU(CA)/g) was adjusted to pH 7.5±0.2 using 10% NaOH solution. 233 g of 15% polyethylene Imine aqueous solution (Sedipur, BASF) and 129 g of disodium hydrogen phosphate were added to the enzyme solution and stirred until dissolution of the disodium hydrogen phosphate. The pH was adjusted back to 7.5±0.2 using 10% NaOH solution
2. 466 g of 15% glutaraldehyde solution were first applied onto 1.9 kg of Sipernat 2200 (silica based carrier from Degussa, Germany) in a 20 L mixer (Lodige, Germany) using continuous mixing with a rotating speed of 150 rpm at ambient temperature. An atomizing nozzle was used, which was adjusted to a 10 min spraying time.
3. Thereafter, the liquid lipase solution (according to 1) was applied on the same silica carrier particles using the same rotating speed and a spraying time of 11 min.
4. The carrier particles were then dried in a fluid-bed using condition described in example 1.
5. After drying and cooling, the liquid enzyme solution containing PEI and $Na_2HPO_4$ (according to 1) was applied to the dried carrier particles.
6. After addition of the liquid enzyme solution in step 5, 466 g of 15% Glutaraldehyde aqueous solution (according to step 2) was applied on the same silica carrier particles using the same rotating speed and a spraying time of 11 min.

After the treatment, the carrier particles were still free flowing individual particles due to the adsorption of the liquid enzyme, PEI and GA onto the carrier particles.

7. The carrier particles were then let stand for 45 min to 16 hr at 5° C.
8. Finally, the immobilized enzyme carrier particles were dried in a fluidized bed (GEA) with inlet temperature 100° C. and were dried until the product temperature reached 60° C. A moisture content below 5% was thus obtained.
Activity of the immobilized enzyme product: 5300 PLU
Enzyme protein leaching measured in DMSO: 5 mg/g
Enzyme protein level before leaching: 50 mg/g Example 4

Immobilization of Lipase on a silica based carrier with an enzyme protein load of 59 mg/g by a 1-step impregnation and subsequent cross-linking by glutaraldehyde (GA)/polyethylene imine (PEI).

1. 1.7 kg of a solution of Lipase B from *Candida Antarctica* (61800 LU(CA)/g) was adjusted to pH 7.5±0.2 using 49 g of a 10% NaOH solution. 834 g of 15% polyethylene Imine (Sedipur, BASF) aqueous solution and stirred for 15 min. pH was then re-adjusted to 7.5±0.2 using 75 g of a 10% NaOH solution.
2. 834 g of 15% glutaraldehyde solution were first applied onto 1.8 kg of Sipernat 2200 (silica based carrier from Degussa, Germany) in a 20 L mixer (Lodige, Germany) using continuous mixing with a rotating speed of 150 rpm at ambient temperature. A pneumatic atomizing nozzle was used, which was adjusted to a 11 min spraying time.
3. Thereafter, the liquid lipase solution (according to 1) was applied on the same silica carrier particles using the same rotating speed and a spraying time of 10 min.
4. After spraying the liquid lipase solution (According to 3), 834 g of 15% Glutaraldehyde aqueous solution was then applied on the same silica particles using the same rotating speed and a spraying time of 12 min.

After the treatment, the carrier particles were still free flowing individual particles due to the adsorption of the liquid enzyme, PEI and GA onto the carrier particles.

5. Finally, the immobilized enzyme carrier particles were dried in a fluidized bed (GEA) with inlet temperature 100° C. and were dried until the product temperature reached 60° C. A moisture content below 5% was thus obtained.
Activity of the immobilized enzyme product: 6400 PLU
Enzyme protein Leaching measured in DMSO: 4 mg/g
Enzyme protein level before leaching: 59 mg/g Example 5

Immobilization of Lipase on a silica based carrier with an enzyme protein load of 50 mg/g by a 1-step impregnation and subsequent cross-linking by glutaraldehyde (GA)/polyethylene imine (PEI). All liquid was added to the silica based carrier in a fluid bed.

5. 894 g of a solution of Lipase B from *Candida Antarctica* (102000 LU(CA)/g) was adjusted to pH 7.5±0.2 using 10% NaOH solution. 221 g of 15% polyethylene imine aqueous solution (Sedipur, BASF) was added to the enzyme solution. 48 g of disodium hydrogen phosphate was dissolved in 1390 g of water and the phosphate solution was added to the enzyme solution. The pH was adjusted back to pH 7.5±0.2 using 10% NaOH solution.

6. The liquid Lipase solution (according to 1) was then applied uniformly onto 2.25 kg of Zeofree 5170 (silica based carrier from Huber Engineered Materials, USA) in a fluid bed (GEA MP-2/3, Germany) using an air flow rate of 125-135 m³/hr and an inlet air temperature of 31° C. The product temperature in the fluid bed was kept at 15-16° C. A nozzle pressure of 1 bar was used, which resulted in a spraying time of 22 min.
7. After addition of the liquid lipase solution (According to 2), 993 g of 6.7% glutaraldehyde aqueous solution (Dow) were then applied on the same silica carrier particles using the same fluid bed and process parameters as given in 2. A spraying time of 15 min. was used.

During the entire process, the carrier particles were free flowing individual particles due to the adsorption of the PEI containing-liquid enzyme solution and GA into the carrier particles.

8. Finally, the carrier particles were dried in the same fluid bed (GEA MP 2/3) with inlet temperature of 100° C. until the product temperature reached 60° C. A moisture content below 5% was thus obtained.
Activity of the immobilized enzyme product: 4200 PLU/g
Enzyme protein leaching measured in DMSO: 6 mg/g
Enzyme protein level before leaching: 50 mg/g Comparison of Example 1, 2, 3, 4 and 5

|  | Process steps | Activity PLU | Enzyme leaching mg/g |
|---|---|---|---|
| Example 1 | Step 1: Lipase on carrier | 3600 | 30 |
| Example 2 | Step 1: Lipase + PEI on carrier<br>Step 2: Addition of glutaraldehyde | 3200 | 13 |
| Example 3 | Step 1: glutaraldehyde on carrier<br>Step 2: Lipase + PEI is added<br>Step 3: drying<br>Step 4: Lipase + PEI is added<br>Step 5: Glutaraldehyde is added. | 5300 | 5 |
| Example 4 | Step 1: glutaraldehyde on carrier<br>Step 2: Lipase + PEI is added<br>Step 3: glutaraldehyde is added. | 6400 | 4 |
| Example 5 | Step 1: Lipase + PEI on carrier<br>Step 2: glutaraldehyde added | 4200 | 6 |

The invention claimed is:

1. A process for producing an immobilized enzyme preparation comprising the following steps:
   a) preparing a first liquid medium by adding a solution of a polyfunctional amine to a liquid comprising an enzyme;
   b) preparing a second liquid medium comprising a cross-linking agent capable of reacting with the polyfunctional amine and the enzyme; and
   c) introducing the first liquid medium onto a particulate porous carrier and then introducing the second liquid medium onto the particulate porous carrier,
   and wherein the amount of first liquid medium and second liquid medium introduced onto the particular porous carrier does not result in the exceeding of the adsorption capacity of the particulate porous carrier for liquid medium, thereby producing an immobilized enzyme preparation.

2. The process of claim 1, wherein the first liquid medium is an aqueous liquid medium.

3. The process of claim 1, wherein the second liquid medium is an aqueous liquid medium.

4. The process of claim 1, wherein introducing the first liquid medium and second liquid medium onto the particulate porous carrier is performed in a mixer, a fluid bed or a pan coater.

5. The process of claim 1, further comprising drying the immobilized enzyme preparation.

6. The process of claim 1, wherein the particulate porous carrier has a particle size of 50 to 1500 μm.

7. The process of claim 1, wherein the first liquid medium and second liquid medium are introduced in an amount such that substantially no agglomeration of the particulate porous carrier occurs.

8. The process of claim 1, wherein introducing the first liquid medium and second liquid medium comprises atomization.

9. The process of claim 1, wherein the particulate porous carrier is selected from the group consisting of silica, zeolite, alumina, diatomaceous earth and kaolin.

10. The process of claim 1, wherein the enzyme is selected from the group consisting of hydrolases, cutinases, oxidases transferases, reductases, hemicellulases, esterases, isomerases, pectinases, lactases, peroxidases, laccases, pectinases, catalases, nitrilases and mixtures thereof.

11. The process of claim 1, wherein the enzyme is a hydrolase selected from the group consisting of proteases, amylases, lipases, phospholipases, esterases, mannanases, cellulases and mixtures thereof.

12. The process of claim 1, wherein the polyfunctional amine is selected from the group consisting of polyethylene imine, polypropylenimine, polyallylamine, polyvinylamine, polymers of 1-amino ethylene with or without N-vinyl formamide, chitosan, albumin, gelatine, spermidine, spermine, triethylentetramine, polypropylene imine dendrimers and bis (2-ethylamino)-1,3-propanediamine.

13. The process of claim 1, wherein the cross-linking agent is selected from the group consisting of glutaraldehyde, polyazetidine, cyanuric chloride, biepoxides and diisocyanates.

14. The process of claim 1, wherein the enzyme is a glucose isomerase.

15. The process of claim 1, wherein the enzyme is a lipase.

* * * * *